Figures 2A, 2B:
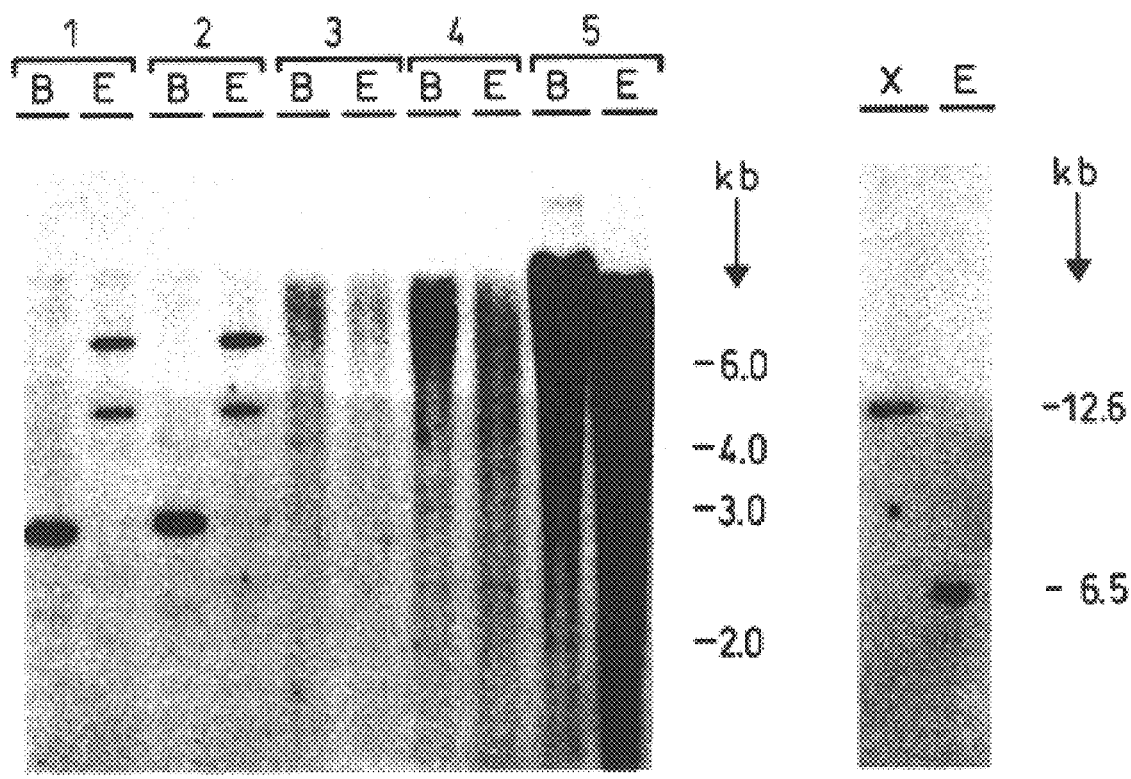

United States Patent
Van Der Straeten et al.

Patent Number: 5,908,971
Date of Patent: Jun. 1, 1999

[54] CRUCIFER ACC SYNTHASE AND USES THEREOF

[75] Inventors: Dominique Van Der Straeten, Gent, Belgium; Howard Goodman, Newton Center, Mass.; Marc Van Montagu, Brussels, Belgium

[73] Assignees: The General Hospital Corporation, Boston, Mass.; Rijksuniversiteit, Gent, Belgium

[21] Appl. No.: 08/463,418

[22] Filed: Jun. 5, 1995

Related U.S. Application Data

[62] Division of application No. 07/962,481, Oct. 15, 1992, abandoned.

[51] Int. Cl.⁶ .............................. A01H 5/00; A01H 5/10; C12N 5/04; C12N 15/82
[52] U.S. Cl. ...................... 800/205; 800/250; 435/69.1; 435/172.3; 435/320.1; 435/419; 536/24.1
[58] Field of Search ................................. 800/205, 250; 435/69.1, 172.3, 240.4, 320.1, 419; 536/23.1, 24.1

[56] References Cited

FOREIGN PATENT DOCUMENTS

| | | |
|---|---|---|
| 0 307 841 | 3/1989 | European Pat. Off. . |
| WO 91/01375 | 2/1991 | WIPO . |
| WO 92/12249 | 7/1992 | WIPO . |
| WO 92/16635 | 10/1992 | WIPO . |
| WO 93/24639 | 12/1993 | WIPO . |

OTHER PUBLICATIONS

Hamilton et al., Nature 346:284–287 (1991).
Van Der Straeten et al., Proc. Natl. Acad. Sci. USA 89:9969–9973 (1992).
Rottmann et al., J. Mol. Biol. 222:937–961 (1991).
Theologis et al., U.S. Application No. 07/579,896, filed Sep. 10,1990.
Van Der Straeten et al., PNAS 87:4859–4863 (1990).
Van Der Straeten et al., Eur. J. Biochem. 182:639–647 (1989).
Park et al., Plant Mol. Biol. 18:377–386 (1992).
Nakajima et al., Plant Cell Physiol. 31:1021–1029 (1990).
Dong et al., Plant Cell Physiol. 32:25–31 (1991).
Nakagawa et al., Plant Cell Physiol. 32:1153–1163 (1991).
Sato et al., J. Biol. Chem. 266:3752–3759 (1991).
Oeller et al., Science 254:437–439 (1991).
Botella et al., Plant Mol. Biol. 18:793–797 (1992).
Huang et al., PNAS 88:7021–7025 (1991).
Olson et al., PNAS 88:5340–5344 (1991).
Goodwin et al. (ed) In: Introduction to Plant Biochemistry, Pergamon Press, Oxford, pp. 616–619 (1983).
Broglie et al., The Plant Cell 1:599–607 (1989).
Roby et al., Plant Physiology 97:433–439 (1991).
Rodrigues–Pousada et al., in "Current Plant Science and Biotechnology in Agriculture", Pech et al., eds., vol. 16, pp. 24–30 (1992).
Rodrigues Pousada et al., The Plant Cell 5:897–911 (1993).
Sato et al., J. Biol. Chem., 266:3752–3759 (1991).
Theologis, Cell 70:181–184 (1992).
Van Der Straeten et al., in "Subcellular Biochemistry", Biswas and Harris, eds., vol. 17, pp. 279–326 (1991).
Kim et al. (1994) Plant Mol Biol 24:105–117.
Benfey et al. (1990) Science 250:959–966.

*Primary Examiner*—Elizabeth F. McElwain
*Attorney, Agent, or Firm*—Clark & Elbing LLP

[57] ABSTRACT

Disclosed is substantially pure DNA encoding a crucifer ACC synthase polypeptide; a promoter functional in immature plant tissues which is capable of ethylene induction; and methods of using such promoters to express recombinant proteins or RNA and to regulate ethylene-inducible events of a plant, e.g., fruit ripening or senescence, especially during early stages of plant development.

18 Claims, 4 Drawing Sheets

Fig. 1A-1

Fig. 1A-2

Fig. 1B

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
    (A) LENGTH: 5613 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:1:

```
GATCCCAAAA AACAATGGGT TCGTTGGTTT TGTTTGAAAG TGTAGATGTA ACGACTCCAA    60

ATAGCCAAAA GTTGATATCT TCAGTCTATA TTATTGAGAT CTTATGTCCC CCCTGTAATT   120

AATTTTTCCA GCAATGCGTG CTTAAAGAAT ATTGTTTGAG ACTTTAGTTA TTGTAATACG   180

ACATTAGTAT AAGTAGAGCC AAAATCAGAT TTTAATATCT TTAGTCTTAA GACATGAAAC   240

AAGATTAAGA AAATACCTTG TTTTCAAAGA AAACGGTTAT AAAAAGGAGG ATTTGAGTTT   300

TTGACATTCA GACGATAAAA ATTATGAACT AGGTCTAGTC ACGTGGTCGA CGCGTGAGAG   360

TTTCCGGCGT GAACTGCAAG TAAAATCACG TAGAGCATGT GATTGACTTG ACCAAAGAGT   420

CCAAACCCAC CAACTACAAA AAAAAATCAA GATATAAATA ACTAACTCTC ACTAGTCACT   480

AATATAATTT TTCATTACAA TTCATATATG ATCTACTAAC AATTGTTGTG GTTATACAAA   540

CAAAAAATTT ATTTTTCGTA AGACGGAAAT TTTGAAATCA AATTCCTCAA CACTCAAATG   600

AATATTCAGT AGTAGTTTAT CAATGACTAG ATTAGATATT TCTTAACGCC AGTCAAATTT   660

TGGAATTATG TGGAGGACGT ACGTTTATAC ATGTGCAGAC TACAACATAC CAAATGTTTT   720

ATTAAACCAA ATTACAATGT TGCAAATTGG TCTATTCTTT TGAATAATCT GATACATTTT   780

ATCTCATAAC TTTCTTCCTT TTTATTTGAA TTCAATCAAA TAATATTCTC CACATCCCCA   840

ACCTTCTTTT TTTTTTTGCA TGACTAAGTA GTTTAAGGTC AACATTTTTC ATAAGAAGTT   900

GCTTAGAAAT AGCCTTGGGT TCAAATAAAA TACACATGAT TTTCCCGTTT CCACCAATAA   960

ATCCCAATGG ATTTTAATAC TGAAACGGAA ATCAATGCGA AACTATTGGA GTAAGACCAA  1020

TTTATTCATC TTAATCTACC AAATTCGATA CGATATGTTT AATACAAGGG AGATTGATGC  1080

TAGCAAAACA CAACCATCTT AATTTTTTTT TTTTTTTTTT AATTAGAAAT TCCCTTCCCA  1140

AATGGTAATT CAATCGTAAC AAAAGTACGT TTTGAAATAT TGTTTTGGAT GGAGATTTTT  1200

TCCTTGGTTC GCTTGTTACT TTTCACTTGT TTCATCAAAT CCTAACTCCT TTTATTTTGG  1260

ACCCCACATC AACTTTATTT GGTCTCCTCA AGGTTTCTGT TTCAACTCCT ATATAAAAGC  1320

AAATAACTCA TACGTTAATT AGTACACACC ACAAAAACTT GTATAAGATC AATATCGATA  1380

CCCCCAAAAA AAAAAAAAAA CAGCTACAAA GAAGTGAGAA TTGACACAGC AAATGGGTCT  1440

TCCGGGAAAA AATAAAGGTG CAGTTTTGTC GAAGATAGCG ACTAACAATC AACACGGAGA  1500

GAACTCAGAG TACTTTGATG GATGGAAAGC TTACGACAAA GATCCTTTTC ATCTTTCCCG  1560

TAACCCCCAT GGGATCATCC AAATGGGTCT TGCAGAGAAT CAGGTACAGA TTATATATAA  1620

TCCAATAAAT CATGTTATAT GTTGTTGTCG TTGTGCATGA ACTTCCATCT ATTAGCTATT  1680

ATATATGAAC ACGTATACAC ATCAAGCTAA TACCTTTTTT TCTTCTTTTC AAGTCAAGTT  1740

AAATACTTAA TAACACATTT TTCTAAACTT CTTACAGCTT TGCTTAGATT TGATCAAAGA  1800

TTGGGTCAAA GAGAACCCAG AAGCTTCTAT TTGCACCCTT GAAGGTATTC ATCAGTTTAG  1860

CGACATCGCT AATTTCCAAG ACTACCATGG TCTTAAGAAG TTTAGACAGG TACTATAAAT  1920

CATTCATTAT TCAGATATCT TGTAATCAGC TACGGACATA TTAGAAAAAC AATTTTTACA  1980

TGGAAAGTTA ATAACACCTC TAAACAATCA GTTGATATGA TCTGCATAAG AAAAACAAAT  2040

TCAGTCGTGG TTTTTTTTTT TTTTTTTTTT TTTTTTTTTT TTTTTTGTTA AAGATTCGTG  2100
```

```
TTGCATTTAA TTAGTAACTT ATTTTATAAA CTTATCCCTA ATATAAATTT TGGAATTGAA    2160

GGCAATTGCA CATTTCATGG GAAAAGCTAG AGGTGGAAGA GTGACTTTTG ATCCGGAGAG    2220

GGTGGTTATG AGCGGAGGAG CCACCGGAGC CAATGAAACA ATCATGTTCT GCCTTGCGGA    2280

TCCCGGCGAC GTTTTCCTCA TTCCCTCCCC GTACTATGCC GCGTAAGCAT TGTTAAAAAC    2340

ATTAATCACA TTTTTAAGAG AAAATAGTAC TAGTATATGA TAATGGATAA TGGTTAGGAC    2400

AGATTTCATT AATGTTACTT TCACATACTT TTTTGGGGTT AACAAATTCT AAATCGAAAT    2460

GAGTTATTAG TATCAAGTTT TGACTCTTTT GCCAAACTTT ATCACACGTG TACGATATAT    2520

CCATTCAATA GCGGTTTTAA TTGAACGACA AGCTCTCATA CGTGTGATAA TTAATGATTT    2580

AATCCTTTCC GCAGATTTGA TAGAGACTTG AGGTGGCGGA CAGGTGTCGA GATAATCCCG    2640

GTTCCTTGTT CAAGCTCCGA CAATTTCAAA TTAACCGTTG ACGCCGCGGA ATGGGCTTAT    2700

AAAAAAGCCC AAGAGTCCAA TAAAAAGTC AAAGGTCTGA TTTTGACCAA CCCATCAAAT     2760

CCACTCGGTA CAATGTTGGA TAAGGACACA CTCACGAACT TGGTCCGGTT TGTCACGAGG    2820

AAGAACATTC ACCTAGTCGT CGACGAGATC TACGCCGCCA CAGTCTTCGC CGGAGGAGAT    2880

TTCGTGAGCG TTGCTGAGGT GGTCAATGAT GTGGACATCT CCGAAGTCAA CGTTGACTTG    2940

ATTCACATTG TCTATAGTCT TTCTAAAGAT ATGGGACTTC CTGGTTTTAG AGTCGGGATA    3000

GTCTATTCTT TCAATGACTC GGTCGTGTCT TGCGCAAGAA AAATGTCAAG TTTCGGACTT    3060

GTTTCGTCTC AGACACAACT CATGCTTGCT TCGATGTTGT CCGATGATCA GTTTGTGGAT    3120

AATTTTCTAA TGGAAAGCTC GAGAAGGTTG GGGATAAGGC ATAAAGTTTT TACCACGGGG    3180

ATCAAGAAAG CAGATATTGC TTGTTTGACA AGCAACGCTG GTTTATTTGC GTGGATGGAT    3240

TTGAGACATC TACTGAGAGA TCGTAACTCG TTTGAATCTG AGATCGAGCT TTGGCATATA    3300

ATCATCGATA GAGTTAAGCT CAATGTGTCT CCTGGCTCTT CCTTCCGTTG CACGGAACCT    3360

GGATGGTTTA GGATTTGCTT TGCCAACATG GACGATGATA CTCTCCATGT GGCGCTTGGA    3420

CGGATCCAAG ATTTCGTGTC TAAGAACAAG AACAAGATCG TCGAGAAAGC ATCTGAAAAT    3480

GATCAGGTAA TCCAGAACAA GAGTGCTAAA AAGCTGAAAT GGACGCAGAC CAATCTTCGA    3540

CTAAGTTTCC GACGACTTTA CGAGGATGGT CTCTCGTCTC CAGGGATAAT GTCACCACAC    3600

TCACCTCTTC TCCGAGCATG AAAATCTTAA GGCATAACGT CTGAGAGATT GGATTAACTC    3660

GTCCGCGTTT CACTCCGTGT TAATTAATCT TAAATTAGTA AGTGATTAAG TAAATGTTTT    3720

TTCTTTCATT GTAAGATTGG AATAATTCAA TTTCGACATT AGGGTTGTTT TTGACGGCCA    3780

GCTTTTTTCC TGGGGTCAAA TGGTAACTTT TAAGATTTTA TGTGTTTGAT TCTGTTTCTT    3840

TTTTCCGCTT AGGATTTTAA TCGATGGATT GTCCTAGTGG TGCTGGTGTG TAGCATATAT    3900

GCTTTTCTTA TATGTTTTTG TGTGTAATAA ATGAAACATT GTCTTTTGAT AAGGATCACC    3960

AGAGTTTATT AGTTGGGGAG GTTGATAATG TTTTGTGAGT AATGGAGGAT TTGTTAACCT    4020

AATTTATTCG ATTTTTTCTA GAACCGCATT TTCTTGTTCG CCCAATACGT CACACGAGCA    4080

TGCCAACATG CCTATCCTTT TTCTAAAATA ATCATTATAT GTACTAAATT GAACATCCGA    4140

TTATACAGAG ATATAATCAA TAAATGCATG TTAAGTTTTA TATCTTGGAA TTTGCCTTAG    4200

CCTATCATAT TGTGGGTGAT GAAAGATTCA TCAGCATTTC AGCTGCACCA AATATGATTA    4260

AATTCAACTT ATTATTTTGT TACAAAGTGA CAAATTTGCT TAGAATAATC AGCTATCAAA    4320

CATGATGACG TCTCCATCAA TTATTCAATA ATCGTCAGCT TTCTTTCCCC TTTTTCTTTG    4380

TTAATGATAA ACCGTCAGCT TGAATGTTAT AGTATTTATT TTTGGTCCTC TTTTGGTAAA    4440

CCATTAGCTA TTATTTGATA AAATTTACAG ATCTCAGATT GATAAATTTG TTACATATAT    4500
```

```
TATATGCTAC TACGACTTTG TTAGGTAATT AAGTGCTGAT GGTAAGGCGT GCTTTGGGCC      4560

GCCTCTTAGC TGATATTGAT ACTACACACA CGAACAAAAA TATATATATA TAAGACAAAA      4620

ATCAAATTTG ATACTTGGAA ACAACGGTTT GATCCTTTTC ACACAGAATA ATATGTATCT      4680

GGATAATATA TAGATATCTC TGTCTAATTA TAATCATCGA CATTATCGTC GTCATCATCA      4740

GTCACAAGTC ACAACCAATT CATGATCATC AACAGTAGGT TACGAAACAT GATCAAGTTA      4800

TATATTTATT TTGTTTGGTA GAAAAAATGA CATGGGCAAG TTTTTTTTTA TATATATATA      4860

GTGAATCCTC TTTTTAATAT TCAAGGGAAC TTTTTTCTGT CTTGGATTTT GTTTGACTC       4920

TAAATAATTC AATACGGCAT AAATTGAAAA TGATGAAATA CCAAATTAAG TTTTCACATG      4980

CTCCTTTTAG GTGGCTACCT ACCAAAATGT TTTTGACATT TGCATTTGGT TTGAGCCACA      5040

ACTTGATCTA TGACATTTAC AATGCACTTG GTTACGTGAA GACTATTTTT AGTAATATAT      5100

CTTTTAACAA AAAAAAAGAT ATATTTTCAA TAATCTTTTG GTGTCGAAAA AGAAAGAAGT      5160

TTGTATGTGG CCGAGATACG GGCATTTTTA TTCTTAAGTG GTTTCTAGAT TTTTTATTTT      5220

TTTTGTTTAG AATAAATTTA GAACTTCACT TTATGCTATT ATCCCCTGAA ATACAGGTAC      5280

ATTTGTGAAG AAACTAAATA AAAATTAGAA CAATTAAAAA CGCTTTACCT TCTCCTCTTA      5340

CAAAATTTCT AAAAGTGACT CATCAGATGA TCATGAAGGC CATGCCCTTT GCTTCGCGCA      5400

AAACAGAAGT AAAGATAAAT TATCAAGTTT ACAGCTGAAA TGTTAATAAG CCGCCCAACA      5460

ACATTTATTC ACCTAAGCTA GCACCCACAT ACATTTAAAA ATATATATAT TGACCAGATT      5520

ATGAAAAAAC TTTGACAATA ACATAGTTAT GAAATATACA TAACCTTAAG AAGAAGATGA      5580

CCAGGTTATG AAATAGCAAA ATCGAATAAA AAC                                  5613
```

(2) INFORMATION FOR SEQ ID NO:2:

(i) SEQUENCE CHARACTERISTICS:
        (A) LENGTH: 496 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

```
Met Gly Leu Pro Gly Lys Asn Lys Gly Ala Val Leu Ser Lys Ile Ala
1               5                   10                  15

Thr Asn Gln His Gly Glu Asn Ser Glu Tyr Phe Asp Gly Trp Lys
            20                  25                  30

Ala Tyr Asp Lys Asp Pro Phe His Leu Ser Arg Asn Pro His Gly Ile
        35                  40                  45

Ile Gln Met Gly Leu Ala Glu Asn Gln Leu Cys Leu Asp Leu Ile Lys
    50                  55                  60

Asp Trp Val Lys Glu Asn Pro Glu Ala Ser Ile Cys Thr Leu Glu Gly
65                  70                  75                  80

Ile His Gln Phe Ser Asp Ile Ala Asn Phe Gln Asp Tyr His Gly Leu
            85                  90                  95

Lys Lys Phe Arg Gln Ala Ile Ala His Phe Met Gly Lys Ala Arg Gly
            100                 105                 110

Gly Arg Val Thr Phe Asp Pro Glu Arg Val Met Ser Gly Gly Ala
        115                 120                 125

Thr Gly Ala Asn Glu Thr Ile Met Phe Cys Leu Ala Asp Pro Gly Asp
    130                 135                 140

Val Phe Leu Ile Pro Ser Pro Tyr Tyr Ala Ala Phe Asp Arg Asp Leu
```

```
                    145                 150                 155                 160
            Arg Trp Arg Thr Gly Val Glu Ile Ile Pro Val Pro Cys Ser Ser Ser
                            165                 170                 175

Asp Asn Phe Lys Leu Thr Val Asp Ala Ala Glu Trp Ala Tyr Lys Lys
                            180                 185                 190

Ala Gln Glu Ser Asn Lys Lys Val Lys Gly Leu Ile Leu Thr Asn Pro
                            195                 200                 205

Ser Asn Pro Leu Gly Thr Met Leu Asp Lys Asp Thr Leu Thr Asn Leu
                            210                 215                 220

Val Arg Phe Val Thr Arg Lys Asn Ile His Leu Val Val Asp Glu Ile
            225                 230                 235                 240

Tyr Ala Ala Thr Val Phe Ala Gly Gly Asp Phe Val Ser Val Ala Glu
                            245                 250                 255

Val Val Asn Asp Val Asp Ile Ser Glu Val Asn Val Asp Leu Ile His
                            260                 265                 270

Ile Val Tyr Ser Leu Ser Lys Asp Met Gly Leu Pro Gly Phe Arg Val
                            275                 280                 285

Gly Ile Val Tyr Ser Phe Asn Asp Ser Val Val Ser Cys Ala Arg Lys
                            290                 295                 300

Met Ser Ser Phe Gly Leu Val Ser Ser Gln Thr Gln Leu Met Leu Ala
            305                 310                 315                 320

Ser Met Leu Ser Asp Asp Gln Phe Val Asp Asn Phe Leu Met Glu Ser
                            325                 330                 335

Ser Arg Arg Leu Gly Ile Arg His Lys Val Phe Thr Thr Gly Ile Lys
                            340                 345                 350

Lys Ala Asp Ile Ala Cys Leu Thr Ser Asn Ala Gly Leu Phe Ala Trp
                            355                 360                 365

Met Asp Leu Arg His Leu Leu Arg Asp Arg Asn Ser Phe Glu Ser Glu
                            370                 375                 380

Ile Glu Leu Trp His Ile Ile Asp Arg Val Lys Leu Asn Val Ser
            385                 390                 395                 400

Pro Gly Ser Ser Phe Arg Cys Thr Glu Pro Gly Trp Phe Arg Ile Cys
                            405                 410                 415

Phe Ala Asn Met Asp Asp Asp Thr Leu His Val Ala Leu Gly Arg Ile
                            420                 425                 430

Gln Asp Phe Val Ser Lys Asn Lys Asn Lys Ile Val Glu Lys Ala Ser
                            435                 440                 445

Glu Asn Asp Gln Val Ile Gln Asn Lys Ser Ala Lys Lys Leu Lys Trp
                            450                 455                 460

Thr Gln Thr Asn Leu Arg Leu Ser Phe Arg Arg Leu Tyr Glu Asp Gly
            465                 470                 475                 480

Leu Ser Ser Pro Gly Ile Met Ser Pro His Ser Pro Leu Leu Arg Ala
                            485                 490                 495

(2) INFORMATION FOR SEQ ID NO:3:

(i) SEQUENCE CHARACTERISTICS:
        (A) LENGTH: 159 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

CAGGCGATTG CGACGTTTAT GGAGAGAGCG AGAGGCGGGC GGGTGAGGTT TGAGGCGGAG      60
```

```
AGGGTGGTGA TGAGCGGAGG AGCCACCGGA GCAAATGAGA CGATCATGTT CTGTCTTGCT      120

GATCCCGGCG ACGCTTTTCT CGTCCCTACT CCTTATTAT                             159
```

(2) INFORMATION FOR SEQ ID NO:4:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

```
Gln Ala Ile Ala Thr Phe Met Glu Arg Ala Arg Gly Gly Arg Val Arg
  1               5                  10                  15

Phe Glu Ala Glu Arg Val Val Met Ser Gly Gly Ala Thr Gly Ala Asn
             20                  25                  30

Glu Thr Ile Met Phe Cys Leu Ala Asp Pro Gly Asp Ala Phe Leu Val
         35                  40                  45

Pro Thr Pro Tyr Tyr
         50
```

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
TATAGTCTTT CTAAAGATAT GGGACTT                                          27
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
GTCGTCGGAA ACTTAGTCGA                                                  20
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
CTCATTCCCT CCCCGTACTA                                                  20
```

(2) INFORMATION FOR SEQ ID NO:8:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:8:

CTCTAAAACC AGGAAGTCCC                                           20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

TCGACTAAGT TTCCCACGAC                                           20

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

GTCGAAATTG AATTATTCCA                                           20
```

CRUCIFER ACC SYNTHASE AND USES THEREOF

This is a divisional of application Ser. No. 07/962,481, filed Oct. 15, 1992 now abandoned.

BACKGROUND OF THE INVENTION

The invention relates to recombinant plant nucleic acids and polypeptides.

The gaseous plant hormone ethylene has a wide impact on plant growth and development (Yang et al., *Ann. Rev. Plant Physiol.* 35:155, 1984). Its synthesis is induced during many stages of plant life including seed germination, leaf abscission, organ senescence, and fruit ripening. Its production also rises strongly upon exposure to various stresses including wounding, excessive temperatures, drought, flooding, and exposure to certain chemicals. Many of these effects are of significant commercial importance in agriculture.

The direct precursor of ethylene in higher plants is the three-membered-ring amino acid 1-aminocyclopropane-1-carboxylic acid. The synthesis of this three-membered-ring amino acid is catalyzed by 1-aminocyclopropane-1-carboxylate synthase (S-adenosyl-L-methionine methylthioadenosine-lyase, EC 4.4.1.14), commonly termed ACC synthase. This synthetic step is the rate-limiting step in the pathway to ethylene production.

SUMMARY OF THE INVENTION

In general, the invention features substantially pure DNA (for example, genomic DNA, cDNA or synthetic DNA) encoding a crucifer (for example, Arabidopsis) ACC synthase polypeptide. In related aspects, the invention also to features a vector, a cell (e.g., a plant cell), and a transgenic plant or seed thereof which includes such a substantially pure ACC synthase DNA. In various preferred embodiments, the cell is a prokaryotic cell, for example, *E. coli* or Agrobacterium, or more preferably, a eukaryotic cell, for example, a transformed plant cell derived from a cell of a transgenic plant.

In a second aspect, the invention features a substantially pure DNA which includes a promoter which is capable of ethylene induction and which is functional in immature plant tissues.

In preferred embodiments, the promoter is an ACC synthase promoter, for example, a crucifer ACC synthase promoter such as the ACC synthase promoter of Arabodopsis. In related aspects, the invention features a transgenic plant containing a transgene which includes such an ethylene-inducible promoter which is functional in immature plant tissue; and a seed and a cell from such a transgenic plant.

In a third aspect, the invention features a transgenic plant containing a transgene which includes a mutant crucifer ACC synthase DNA sequence; and a seed and cell from such a transgenic plant.

In a fourth aspect, the invention features a method of producing a recombinant crucifer ACC synthase polypeptide which involves: (a) providing a cell transformed with DNA encoding a crucifer ACC synthase polypeptide positioned for expression in the cell; (b) culturing the transformed cell under conditions for expressing the DNA; and (c) isolating the recombinant crucifer ACC synthase polypeptide.

In a fifth aspect, the invention features a method of inhibiting an ethylene-inducible event in a plant which involves: (a) providing a transgenic plant with DNA encoding a crucifer ACC synthase polypeptide positioned for expression in a cell of said plant; and (b) culturing the transgenic plant under conditions for expressing the DNA. In preferred embodiments, the events inhibited include fruit ripening, fruit maturation, senescence, and/or cell development.

In a sixth aspect, the invention features a method of inducibly producing a compound in a cell which involves: providing a cell which includes DNA encoding the compound operably linked to an ethylene-inducible promoter which is functional in immature plant tissue; and administering ethylene to the cell to induce compound production.

In a preferred embodiment, the method may further involve isolating the compound.

In other preferred embodiments, the compound is a recombinant protein, a protein normally produced by the cell, or an RNA molecule; the cell is a plant cell; the cell is obtained from a transgenic plant which includes one or more cells which contain the ethylene-inducible promoter of the invention as a transgene.

In a final aspect, the invention features substantially pure crucifer ACC synthase polypeptide. Preferably, the polypeptide includes a sequence substantially identical to an amino acid sequence shown in FIG. 1 (SEQ ID NOS: 2 and 4). Most preferably, the polypeptide is a crucifer ACC synthase polypeptide, for example, the Arabidopsis ACC synthase polypeptide.

By "crucifer" is meant any plant that is classified within the Cruciferae family as commonly described in, e.g., Gray's Manual of Botany American Book company, N.Y., 1950; *Hortus Third: A Concise Dictionary of Plants Cultivated in the U.S. and Canada*, Macmillan, 1976; or Simmons, N. W., *Evolution of Crop Plants*, 1986. The Cruciferae include many agricultural crops, including, broccoli, cabbage, brussel sprouts, rapeseed, kale, Chinese kale, cauliflower, horseradish and Arabidopsis.

By "ACC synthase" is meant an ACC synthase polypeptide capable of the enzymatic conversion of AdoMet(S-adenosylmethionine) to ACC (1-aminocyclopropane-1-carboxylic acid) and MTR (5-methylthioribose) as described by Yang et al., supra.

By "polypeptide" is meant any chain of amino acids, regardless of length or post-translational modification (e.g., glycosylation or phosphorylation).

By "substantially identical" is meant a polypeptide or nucleic acid exhibiting at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant an ACC synthase polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, ACC synthase polypeptide. A substantially pure ACC synthase polypeptide may be obtained, for example, by extraction from a natural source (e.g., a plant cell); by expression of a recombinant nucleic acid encoding an ACC synthase polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or CDNA fragment produced by PCR or restriction endonuclease digestion) independent of other sequences. It also includes a recombinant DNA which is part of a hybrid gene encoding additional polypeptide sequence.

By "mutant form of ACC synthase polypeptide" is meant a polypeptide which includes any change (in comparison to the wild-type) in the DNA sequence. These changes can arise, e.g., spontaneously by chemical energy, e.g., X-ray, or by other forms of mutagenesis, by genetic engineering, or as a result of mating or other forms of exchange of genetic information. Mutations include, e.g., base changes, deletions, insertions, inversions, translocations, or duplications. Such mutant forms of ACC polypeptides display an inactive or attenuated ACC synthase enzymatic activity, as measured by standard ACC synthase activity assays (e.g., Yu et al., Arch. Biochem. Biophys. 198: 280, 1979; Lizada et al., Anal. Biochem. 100: 140, 1979; or Van Der Straeten et al., Eur. J. Biochem. 182:639, 1989). Preferably, such mutant ACC synthase polypeptides have (a) significantly (i.e., at least 25%) decreased activity compared to the wild-type form, or (b) have significantly (i.e., at least 25%) decreased polypeptide production (e.g., by Western blot assay) as compared to the wild-type cell.

By "transformed cell" is meant a cell into which (or into an ancestor of which) has been introduced, by means of recombinant DNA techniques, a DNA molecule encoding (as used herein) an ACC synthase polypeptide.

By "positioned for expression" is meant that the DNA molecule is positioned adjacent to a DNA sequence which directs transcription and translation of the sequence (i.e., facilitates the production of, e.g., an ACC synthase polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression inducible by ethylene in immature plant tissue; such elements may be located in the 5' or 3' regions of the native gene.

By "immature plant tissue" is meant any tissue of the plant obtained between seed imbibition and germination, and the production of flowers.

By "operably linked" is meant that a gene and a regulatory sequence(s) are connected in such a way as to permit gene expression when the appropriate molecules (e.g., transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome.

By an "ethylene inducible promotor" is meant a promoter whose level of activity is increased in response to treatment with ethylene or an equivalent compound such as propylene.

Other features and advantages of the invention will be apparent from the following description of the preferred embodiments thereof, and from the claims.

DETAILED DESCRIPTIONS

The drawings will first be described.

DRAWINGS

FIG. 1 shows the nucleotide and deduced amino acid sequences of the *A. thaliana* ACC synthase gene (AThACC1) (SEQ ID NO: 1 and 2) and partial cDNA (AThACC2 (SEQ ID NO: 3). (A) DNA and amino acid sequences of AThACC1 (SEQ ID NOS: 1 and 2). Exons are in upper case letters; noncoding regions are in lower case letters. The G box core element, the putative CAAT and TATA boxes, and polyadenylation signals are boxed. The region of highest similarity with other ACC synthase promoters, containing a short inverted repeat, is underlined, as well as long thymine and adenine stretches. Deduced amino acids are in the one letter code. The active site region is boxed. (B) DNA and amino acid sequences of the AThACC2 cDNA (SEQ ID NOS: 3 and 4).

FIGS. 2A–2B shows a genomic DNA gel blot analysis of *A. thaliana, Oryza sativa* (Cv. Taipei), *Lycopersicon esculentum* (Cv. Orlando), and *Nicotiana tabacum*. Panel A from left to right: *A. thaliana* (ecotype C24), 1 μg total DNA; *A. thaliana*, 1 μg nuclear DNA; rice, 3 μg nuclear DNA; tomato, 5 μg total DNA; tobacco, 20 μg nuclear DNA. DNA was digested with BglII (B) or EcoR1 (E). The filter was hybridized at 65° C. with a $^{32}$P-labeled 2.2-kb BamHI fragment of the AThACC1 gene. Exposure was for 12 hours on flash-sensitized film. Panel B shows from left to right: *A. thaliana* (ecotype Lansberg erecta) XbaI and EcoR1 digest. The filter was hybridized at 60° C. with a PCR fragment 3,540–3,905 base pairs, most of which covered the 3' untranslated region. Exposure was for 5 days on flash-sensitized film.

FIG. 3 is a reverse transcription-PCR analysis of the AThACC1 gene on total RNA from different organs of Arabidopsis and from mature plants after ethylene exposure. In Panel A PCR analysis was carried out using a primer specific for AThACC1 (PCR3 and PCR14). Lane 1, 500 base pair marker; lane 2, young leaves; lane 3, roots; lane 4, flowers; lane 5, mature green siliques; lane 6, ripe siliques; lane 7, etiolated seedlings; lane 8, mature plants; lane 9, as in 8, but after two hours of ethylene exposure; lane 10, four hours; lane 11, eight hours; lane 12, 12 hours of ethylene exposure. In Panel B PCR analysis was carried out as in Panel A but with nonspecific primers (PCR19 and PCR20). Lanes are numbered as for Panel A.

FIG. 4 is a reverse transcription-PCR analysis of expression of the AThACC1 gene performed on total RNA from wounded, young Arabidopsis leaves. In Panel A, PCR analysis was carried out using a primer specific for ATHACC1 (PCR22 and PCR24). Lane 1, young leaves; lane 2, after 30 minutes wounding; lane 3, 60 minutes; lane 4, 90 minutes; lane 5, 2 hours; lane 6, 3 hours; lane 7, 4 hours; lane 8, 8 hours; lane 9, control on 5 ng cosmid DNA carrying AThACC1. In Panel B PCR analysis was carried out as in Panel A but with nonspecific primers (PCR19 and PCR20). Lanes are numbered as for Panel A.

There now follows a description of the cloning and characterization of an Arabidopsis ACC synthase genomic DNA and CDNA useful in the instant invention. This example is provided for the purpose of illustrating the invention, and should not be construed as limiting.

Isolation of Arabidopsis ACC Synthase Genomic DNA and cDNA

A cosmid library of *A. thaliana* (ecotype Columbia) constructed by standard techniques was screened (also by standard techniques) using degenerate oligonucleotides derived from a tomato ACC synthase peptide sequence (Van Der Straeten et al., supra). Isolated genomic sequences were subcloned into the pUC18 plasmid, and DNA sequence analysis was performed by the Sanger method. The library screening led to the isolation of the AthACC1 gene and its identification by similarity to other ACC synthases.

FIG. 1A presents the genomic sequence of the AthACC1 gene (5613 bp (SEQ ID NO: 1). The sequence covers 1432 bp upstream from the initiation codon and 1993 bp downstream from the stop codon. Putative CAAT and TATA boxes (Joshi, Nucl. Acids Res. 15:6643 (1987), as well as the potential polyadenylation site (Dean et al., Nucleic Acids Res. 14:2229, 1986), are indicated. The gene contains three introns; consensus dinucleotides are located at their boundaries (Csank et al., Nucleic Acids Res. 18:5133, 1990). The position of the exon-intron junctions are identical to those in the tomato ACC synthase genes (Rottmann et al., J. Mol. Biol. 222:937, 1991). When comparing the promoter region of AthACC1 with the promoter of the CPACC1A encoding gene of zucchini (Huang et al., Proc. Natl. Acad. Sci. USA, 88:7021, 1991), the highest similarity was found in the region from 525 to 730. Interestingly, this region is partially overlapping with the region of highest similarity with the *Lycopersicon esculentum* LE-ACC2 promoter (Yip et al., Proc. Natl. Acad. Sci. USA, 81:2475, 1992) 661–827 bp in AThACC1). A 13-bp-long sequence in AThACCI (903–915) was also found in the fourth exon of the zucchini gene and with 77% similarity, far upstream, in the promoter of the LE-ACC2 gene. Comparison of the AThACCI promoter with other ethylene-responsive promoters (Van Der Straeten et al., *Plant Genetic Engineering*, eds., Biswas, B. B. and Harris, J. R., Plenum, N.Y. pp. 279–326, 1991) revealed significant similarity (70–80%) in several short stretches of the 5' region. The wound-inducible promoters, winla (Stanford et al., Mol. Gen. Genet., 215:200, 1989) and wunla (Logeman et al., Mol. Gen. Genet. 219:81, 1989), were 91% similar to AThACCI in the regions 918–929 bp and 1170–1180 bp, respectively. No significant similarities with auxin-responsive elements were found. It is worth noting that a myc-like binding site (Blackwell et al., Science 230:1149, 1990) resembling the G-box core is present at position 340, found in several light-regulated promoters (Giuliano et al., Proc. Natl. Acad. Sci. USA 85:7089, 1988; Schulze-Lefert et al., EMB0 J. 8:651, 1989), in the abscisic acid response element of the wheat Em gene (29), and in the LE-ACC2 promoter (Rottmann et al., supra). In addition, both the 5'-untranslated region and intron 2 of AThACCI contain long thymine (Kosambi, Ann. Eugen. 12:172, 1944, 36 nucleotides) and adenine stretches (15 nucleotides, close to the start codon).

As indicated in FIG. 1, the genomic clone AthACC1, encodes a polypeptide of 496 amino acids. This polypeptide has a predicted molecular mass of 54.6 kDa and a Pi of 7.3. The 12 amino acids of the active-site region are identical to those of tomato (TACCI or pCVV4A; Van Der Straeten et al., supra), winter squash (Nakajima et al., Plant Cell Physiol 31:1021, 1991), and zucchini (Sato et al., J. Biol. Chem. 266:3752, 1991) ACC synthases. Moreover, in all ACC synthases so far cloned, 11 of the 12 amino acids involved in the binding of the substrate and the cofactor of amino transferases are conserved. This result supports the hypothesis that ACC synthases and aminotransferases are evolutionary related (Rottman et al., supra). Table I gives an overview of the amino acid and nucleotide sequence similarities of ACC synthases from various species of which full-length clones have been isolated.

TABLE I

| Enzyme | | Nucleotide Identity, % | Amino Acid Identity, % | Ref. |
|---|---|---|---|---|
| TACC1 | (tomato) | 68 | 75 | Van Der Straeten et al., Proc. Natl. Acad. Sci., USA, 87:4589, 1190 |
| TACC2 | (tomato) | 66 | 71 | Olson et al. Proc. Natl. Acad. Sci., USA, 88:5340, 1991 |
| CMW33 | (winter squash) | 67 | 71 | Nakajima et al., Plant Cell Physiol., 31:1021, 1990 |
| CMA101 | (winter squash) | 68 | 64 | Nakagawa et al., Plant Cell Physiol., 32:1153, 1991 |
| CPACCIA | (zucchini) | 67 | 72 | Huang et al., Proc. Natl. Acad. Sci., USA, |

TABLE I-continued

| Enzyme | | Nucleotide Identity, % | Amino Acid Identity, % | Ref. |
|---|---|---|---|---|
| CARACC3 | (carnation) | 65 | 73 | 88:7021, 1991 Park et al., Plant Mol. Biol. 18:388, 1992 |

A flower-specific cDNA library of ecotype C24 was constructed using standard techniques. The library was screened (also using standard techniques) with a 2.2-kilobase (kb) BamH1 fragment of the *A. thaliana* ACC synthase cDNA (AthACC1) gene covering the first 140 amino acids of the coding region and the two first introns.

Figures 1A-2, 1B:
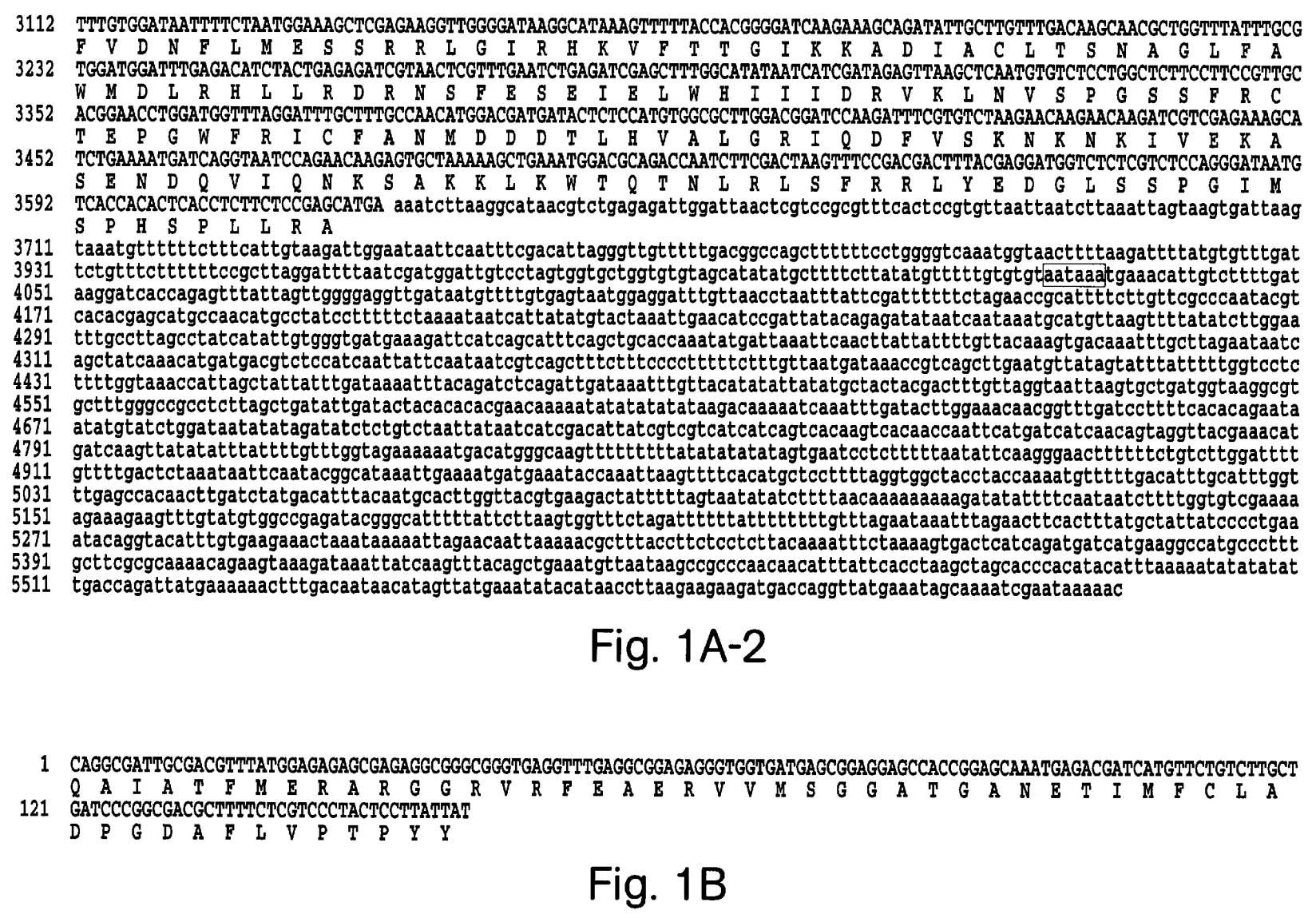

A partial cDNA of another Arabidopsis ACC synthase gene was isolated from a flower-specific cDNA library using a 2.2-kb BamHI fragment of AthACC1 as a probe and was designated AthACC2. Its sequence is shown in FIG. 1B (SEQ ID NO: 2). The 159 nucleotides are 79% identical to the corresponding region of AthACC1. This level of sequence difference cannot be readily accounted for by the difference in ecotypes (Columbia vs. C24). Deduced amino acids in this region are 83% identical.

Arabidopsis ACC Synthase Multigene Family and Its Relationship to Other Plant ACC Synthase Genes The existence of several ACC synthase genes in Arabidopsis was confirmed by genomic DNA gel blots (FIG. 2). The ATHACCI gene is a member of the ACC synthase gene family but without high similarity to any other member. Hybridization of the AthACC1 2.2-kb BamHI fragment to both total and nuclear Arabidopsis DNA under high-stringency conditions revealed a BglII fragment at 2.7 kb and two EcoRI fragments of 5.0 and 6.5 kb, each with half the intensity of the BglII band (FIG. 2A). This is a single gene pattern corresponding to the restriction map of AthACC1. Confirmation was obtained by hybridizing Arabidopsis genomic DNA with the 1.1-kb BamHI fragment (covering approximately 75% of the coding region); as well as with a 350 bp PCR generated fragment, the sequence of which resides mostly in the 3' untranslated region (FIG. 2B). In the latter cases a single band was observed at 6.5 kb in the EcoRI and at 12 kb in the XbaI lanes. However, when repeated under low-stringency conditions (53° C.) with the 2.2- and 1.1-kb BamHI fragments covering the coding region as probes, several extra bands became apparent, indicating the existence of related members of the ACC synthase gene family. In addition, it could be concluded that AthACCI is relatively divergent from ACC synthases in rice, tomato, and tobacco, because no cross-hybridization was visible under high stringency conditions (FIG. 2A), whereas faint bands appeared under lower stringency.

From the aforementioned description and the nucleic acid sequence shown in FIG. 1, the isolation of any crucifer cDNA encoding an ACC synthase polypeptide is easily accomplished through the use of standard hybridization screening techniques (see, e.g., Ausubel et al., *Current Protocols in Molecular Biology*, John Wiley & Sons, 1989).

Restriction Fragment Length Polymorphism (RFLP) Mapping of the AthACC1 Gene

RFLP mapping analysis was done by the procedure detailed by Nam et al., Plant Cell 1:699, 1989, using the cosmid carrying the AthACC1 gene as a probe. Segregation data were analyzed with the MAPMAKER computer program (Lander et al., Genomics 1:174, 1987), and the maximum likelihood recombination fractions for each pair of adjacent markers were transformed into centimorgan distances with the Kosambi function (Kosambi, supra).

Using the restriction enzyme ClaI, one Columbia polymorphic band and one Landsberg erecta polymorphic band showed appropriate segregation and mapped to the same locus. This RFLP has been designated pvv4 and maps to the telomere proximal region at the top of chromosome 1 at 0.0 centimorgans on a revised RFLP. It is 37.4 centimorgans above (telomere proximal) RFLP 5972 (which mapped at 0.0) in the published map of Nam et al. (supra).

Study of Expression of AThACC1 as Determined by Reverse Transcription-Polymerase Chain Reaction (RT-PCR)

*A. thaliana* (ecotype C24) plants were grown at 22° C. and 60% relative humidity under white-fluorescent light (photoperiod 16 hr light/8 hr dark, at a fluence rate of 75 $\mu mol.m^{-2}.s^{-1}$). Young leaves from 3- to 5-week-old plants were wounded with a scalpel. Senescent leaves were from 8- to 12-week-old plants. Flower samples contained only flowers with white, non-senescing petals. Mature-ripe siliques presented a yellow to light-brown coloration and had mature seeds. Mature-green siliques did not show any sign of chlorophyll loss. Flowering *A. thaliana* plants (6- to 8-week old) were either immediately frozen or, for ethylene inductions, placed in a sealed container and subjected to a continuous flow of 9 liter/hr of ethylene at 10 ppm for 2–12 hr. Auxin treatments were done by soaking 7-day old light grown seedlings in 0.5 mM indoleacetic acid (IAA) in 50 mM sodium phosphate buffer, pH 7.0, for 4 hr.

Total RNA was isolated as reported (Rodriquez-Pousada et al., Technique 2:292, 1990). RT-PCR was done as in Goblet et al., Nucleic Acids Res. 17:2144, 1989, with minor modifications. In summary, 10 $\mu g$ of total RNA (accurately quantified) was mixed with the 3' oligonucleotide in 50 $\mu l$ of 1X buffer (67.2 mM Tris-HCl (pH 8.8), 16.6 mM $(NH_4)_2SO_4$, 2 mM $MgCl_2$, bovine serum albumin (nuclease free) at 1.68 mg/ml, 0.72% 2-mercaptoethanol) and incubated at 85° C. for 5 min, followed by 5 min at 45° C. The tubes were put on ice and 50 $\mu l$ of a reaction mixture containing the 5' oligonucleotide, 1X buffer, 2.5 units of Taq polymerase (Beckman, Somerset, N.J.), 16 units of avian myeloblastosis virus reverse transcriptase (Promega, Madison, Wis.), 20 units of RNasin (Promega), and 0.2 mM of each DNTP were added. Reverse transcription was done by incubating the tubes at 40° C. for 45 min immediately followed by the PCR reaction; 30–35 cycles of 1.5 min at 94° C., 1.5 min at 50° C. and 45 min at 72° C. Reactions were done in a PHC-2 thermocycler (Techme, Cambridge, U.K.).

The PCR products were analyzed by 0.8–1% agarose/TAE gel electrophoresis and blotted on Hybond-N membrane. Three pairs of oligonucleotides were used as primers:

Pair 1:

| PCR14 | 5' TATAGTCTTTCTAAAGATATGGGACTT 3' | (bp 2953–2979) | (SEQ ID NO: 5) |
|---|---|---|---|
| PCR3 | 5' GTCGTCGGAAACTTAGTCGA 3' | (bp 2297–2316) | (SEQ ID NO.: 6); |

-continued

Pair 2 (covering highly conserved regions, non-specific):

| PCR20 | 5' CTCATTCCCTCCCCGTACTA 3' | (bp 2297–2316) | (SEQ ID NO: 7) |
| PCR19 | 5' CTCTAAAACCAGGAAGTCCC 3' | (bp 2992–2973) | (SEQ ID NO: 8); |

Pair 3 (specific for AthACCI):

| PCR22 | 5' TCGACTAAGTTTCCCACGAC 3' | (bp 3537–3556) | (SEQ ID NO: 9) |
| PCR24 | 5 GTCGAAATTGAATTATTCCA 3' | (bp 3758–3738) | (SEQ ID NO: 10). |

All data are the result of two independent experiments.

Figure 3A:
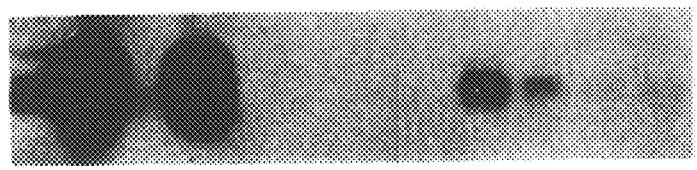
Figure 3B:
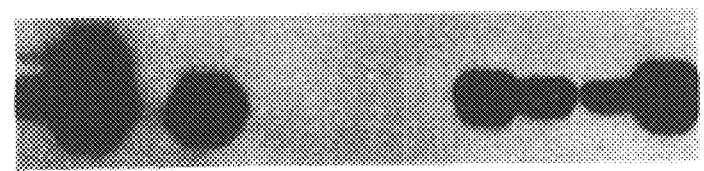

Due to the lack of sensitivity of Northern (RNA) blotting in detecting very low abundance mRNAs (as AThACC1 mRNAs), RT-PCR was used for analysis of mRNA levels (Deiidow et al., Gene Anal. Techn. 11:636, 1989; Buck et al., BioTechniques 11:636, 1991). To allow quantitative comparison within each experiment, the number of PCR cycles was kept low. In certain cases Northern blots were done with a probe predicted to produce constant signals under given induction conditions. Different sets of oligonucleotides derived from the coding sequences or the 3'-untranslated region of the AThACC1 gene were synthesized to monitor levels of all ACC synthase mRNAs or AThACC1 mRNA alone. FIG. 3 presents a DNA gel blot of a RT-PCR reaction on different total RNA samples using primers PCR3 and PCR14, which most likely specifically amplify AthACC1 cDNA because primer PCR3 resides in the 3' end of the coding region where ACC synthases are known to be highly divergent. The signal was very high in young leaves and in flowers but barely visible in roots and absent in siliques and etiolated seedlings (FIG. 3A, lanes 1–7). The same pattern was found when the conserved oligonucleotides PCR19 and PCR20 were used (FIG. 3B, lanes 1–7).

When mature plants were exposed to a continuous flow of ethylene at 10 ppm, an early induction could be seen (2 hr, FIG. 3A, lane 9) but the induction almost returned to basal level after 8 hr (lane 11). Remarkably, control plants did not show any signal (FIG. 3A, lane 8). The same pattern was observed when oligonucleotide pair 3 was used. When mature plants were exposed to a continuous flow of 10 ppm ethylene, an early induction occurred; a first peak occurred at 2 hr, and a second, strong induction occurred at 12 hr. Exposure of 7-day-old light-grown seedlings to indoleacetic acid did not lead to any significant induction of the AThACC1 gene.

Figure 4A:
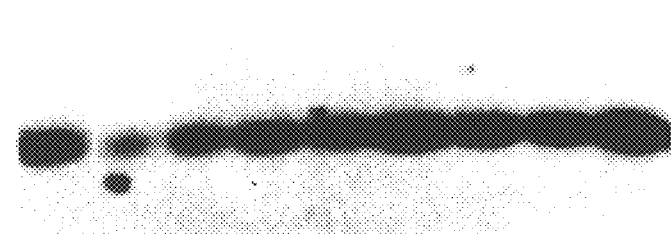
Figure 4B:
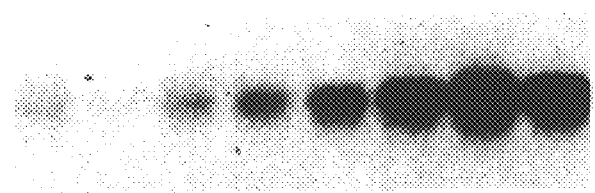

In FIG. 4, the effect of wounding on *Arabidopsis thaliana* ACC synthase mRNA levels is shown. FIG. 4A presents a DNA gel blot of samples treated with the oligonucleotide pair 3, which specifically amplifies AthACC1 mRNA. The signals obtained between 30-min and 8-hr wounding did not vary significantly. However, a clear induction was seen when the nonspecific set of oligonucleotides was used (pair 2); a peak occurred 4 hr after wounding (FIG. 4B).

Thus, in general, we describe the cloning of a gene encoding a member of the *A. thaliana* ACC synthase gene family (AthACC1) and one partial cDNA corresponding to another ACC synthase (AthACC2). The existence of a multigene family in Arabidopsis was confirmed by genomic DNA gel blots that also indicate that the AthACC1 gene is distantly related to other family members. An analysis of the promoter sequence revealed similarities with several other promoters. Most noteworthy was the homology with the promoter of the tomato ACC synthase LE-ACC2 gene (Rottman et al., supra) and the zucchini CP-ACC1a gene (Huang et al., supra), in the region 661–730 bp. In addition a G-box core element was found far upstream (340–345 bp). In both cases, their possible involvement in gene regulation remains to be provided. Comparison of the predicted amino acid sequence with other ACC synthase proteins revealed the same common features presented earlier (Dong et al., Plant Cell Physiol. 32:25, 1991), and similarities ranged between 71 and 75% (Table I).

The exact mechanisms underlying ethylene biosynthesis by induction of ACC synthase genes is unclear. From physiological data (Yang et al., supra), it can be argued that at least three classes of ACC synthases could exist—one ripening and senescence-related, one auxin-induced, and one stress-induced. However, a recent report on ACC synthase genes in tomato has indicated that the individual genes are not assigned to only one function (Yip et al., supra). The data presented here support the existence of a complex regulatory pattern of the ACC synthase gene family in Arabidopsis. The AthACCI gene was expressed prominently in young leaves and flowers but was not expressed in leaves of mature plants nor in mature green or ripe siliques (FIG. 3). The AthACC1 gene was also shut down in rosette leaves with the onset of the reproductive phase. Interestingly, AthACC1 mRNA levels seemed to be influenced by ethylene itself. Upon ethylene exposure of mature plants, the AthACC1 mRNA accumulated after 2 hr., whereas the ACC synthase gene family showed a biphasic activation with peaks after 2 and 12-hr treatment (FIG. 3). Although the AthACC1 gene appeared to be switched off in senescent leaves, it remains to be determined whether it has any role in the onset of senescence or in the early senescence phase remains to be determined. In addition, AthACC1 was shown not to be wound-inducible, at least not in young tissue. This contrasted with the pattern of accumulation observed for the ACC synthase mRNAs in general, where a peak was detected after 4 hr (FIG. 4).

ACC Synthase Polypeptide Expression

Polypeptides according to the invention may be produced by transformation of a suitable host cell with all or part of an ACC synthase cDNA (e.g., the cDNA described above) in a suitable expression vehicle.

Those skilled in the field of molecular biology will understand that any of a wide variety of expression systems may be used to provide the recombinant protein. The precise host cell used is not critical to the invention. The ACC synthase polypeptide may be produced in a prokaryotic host, e.g., *E. coli*, or in a eukaryotic host, e.g., *Saccharomyces cerevisiae*, mammalian cells (e.g., COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include Chlamydomonas, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Rice, Corn, Millet, Onion, Barley, Orchard grass, Oat, Rye, and Wheat.

Such cells are available from a wide range of sources including: the American Type Culture Collection (Rockland, Md.); Chlamydomonas Culture Collection, (Duke University), Durham, N.C.; or from any of a number seed companies, e.g., W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I.K., *Cell Culture and Somatic Cell Genetics of Plants*, Vol I, II, III Laboratory Procedures and Their Applications Academic Press, New York, 1984; Dixon, R. A., *Plant Cell Culture-A Practical Approach*, IRL Press, Oxford University, 1985; Green et al., *Plant Tissue and Cell Culture*, Academic Press, New York, 1987; Gasser and Fraley, Science 244:1293, 1989.

For prokaryotic expression, DNA encoding an ACC synthase of the invention is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors may be found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., Nature 198: 1056, 1977), the tryptophan (Trp) (Goeddel et al., Nucl. Acids Res. 8: 4057, 1980) and the tac promoter systems as well as the lambda-derived $P_L$ promoter and N-gene ribosome binding site (Simatake et al., Nature 292:128, 1981).

For eukaryotic expression, the method of transformation or transfection and the choice of vehicle for expression of the ACC synthase will depend on the host system selected. Transformation and transfection methods are described, e.g., in Ausubel et al. (supra); Weissbach and Weissbach, *Methods for Plant Molecular Biology*, Academic Press, 1989; Gelvin et al., *Plant Molecular Biology Manual*, Kluwer Academic Publishers, 1990; Kindle, K., *Proc. Natl. Acad. Sci.*, USA 87:1228, 1990; Potrykus, I., *Annu. Rev. Plant Physiol. Plant Mol. Biology* 42:205, 1991; and BioRad (Hercules, Calif.) Technical Bulletin #1687 (Biolistic Particle Delivery Systems). Expression vehicles may be chosen from those provided, e.g., in *Cloning Vectors*: A Laboratory Manual (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

One preferred eukaryotic expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an ACC synthase polypeptide would be inserted into the pMAMneo vector in an orientation designed to allow expression. The recombinant ACC synthase protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, an ACC synthase polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the ACC synthase polypeptide is cloned into an expression vector which includes the dihydrofolate reductase (DHFR) gene. Integration of the plasmid and, therefore, the ACC synthase-encoding gene into the host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV (A) (described in Ausubel et al., supra). Any of the host cells described above or, preferably, a DHFR-deficient CHO cell line (e.g., CHO DHFR$^-$cells, ATCC Accession No. CRL 9096) are among the host cells preferred for DHFR selection of a stably-transfected cell line or DHFR-mediated gene amplification.

Most preferably, an ACC synthase polypeptide is produced by a stably-transfected plant cell line or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weisbach (supra), and Gelvin et al. (supra). Typically, plant expression vectors include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific expression), a transcription initiation start site, a ribosome binding site, an RNA processing signal, a transcription termination site, and/or a polyadenylation signal.

An example of a useful plant promoter according to the invention is a caulimovirus promoter, e.g., a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., Nature 313: 810, 1985). The CaMV promoter is also highly active in monocots (see, e.g., Dekeyser et al., Plant Cell 2:591, 1990; Terada and Shimamoto, Mol. Gen. Genet. 220:389, 1990). Moreover, activity of this promoter can be further increased (i.e., between 2–10 fold) by duplication of the CaMV 35S promoter (see e.g., Kay et al., Science 236:1299, 1987; Ow et al., Proc. Natl. Acad. Sci., USA 84: 4870, 1987; and Fang et al., Plant Cell 1: 141, 1989).

Other useful plant promoters include, without limitation, the nopaline synthase promoter (An et al., Plant Physiol. 88:

547, 1988) and the octopine synthase promoter (Fromm et al., Plant Cell 1: 977, 1989).

For certain applications, it may be desirable to produce the ACC synthase gene product in an appropriate tissue, at an appropriate level, or at an appropriate developmental time. Thus, there are an assortment of gene promoters, each with its own distinct characteristics embodied in its regulatory sequences, shown to be regulated in response to the environment, hormones, and/or developmental cues. These include gene promoters that are responsible for (1) heat-regulated gene expression (see, e.g., Callis et al., Plant Physiol. 88: 965, 1988), (2) light-regulated gene expression (e.g., the pea rbcS-3A described by Kuhlemeier et al., Plant Cell 1: 471, 1989; the maize rbcs promoter described by Schaffner and Sheen, Plant Cell 3: 997, 1991; or the cholorphyll a/b-binding protein gene found in pea described by Simpson et al., EMBO J. 4: 2723, 1985), (3) hormone-regulated gene expression (e.g., the abscisic acid responsive sequences from the Em gene of wheat described Marcotte et al., Plant Cell 1:969, 1989), (4) wound-induced gene expression (e.g., of wunI described by Siebertz et al., Plant Cell 1: 961, 1989), or (5) organ-specific gene expression (e.g., of the tuber-specific storage protein gene described by Roshal et al., EMBO J. 6:1155, 1987; the 23-kDa zein gene from maize described by Schernthaner et al., EMBO J. 7: 1249, 1988; or the French bean β-phaseolin gene described by Bustos et al., Plant Cell 1:839, 1989).

Plant expression vectors may also optionally include RNA processing signals, e.g, introns, which have been shown to be important for efficient RNA synthesis and accumulation (Callis et al., Genes and Dev. 1: 1183, 1987). The location of the RNA splice sequences can dramatically influence the level of transgene expression in plants. In view of this fact, an intron may be positioned upstream or downstream of an ACC synthase polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl Acad. Sci USA 84: 744, 1987; An et al., Plant Cell 1: 115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/ml (kanamycin), 20–50 μg/ml (hygromycin), or 5–10 μg/ml (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals and terminator elements, but also on how these elements are used to increase the levels of selectable marker gene expression.

Plant Transformation

Upon construction of the plant expression vector, several standard methods are accessible for introduction of the recombinant genetic material into the host plant for the generation of a transgenic plant. These methods include (1) Agrobacterium-mediated transformation (A. tumefaciens or A. rhizogenes) (see, e.g., Lichtenstein and Fuller In: *Genetic Engineering*, vol 6, PWJ Rigby, ed, London, Academic Press, 1987; and Lichtenstein, C. P., and Draper, J,. In: *DNA Cloning*, Vol II, D. M. Glover, ed, Oxford, IRI Press, 1985), (2) the particle delivery system (see, e.g., Gordon-Kamm et al., Plant Cell 2:603, 1990; or BioRad Technical Bulletin 1687, supra), (3) microinjection protocols (see, e.g., Green et al., supra), (4) polyethylene glycol (PEG) procedures (see, e.g., Draper et al., Plant Cell Physiol 23:451, 1982; or e.g., Zhang and WU, Theor Appl Genet 76:835, 1988), (5) liposome-mediated DNA uptake (see, e.g., Freeman et al., Plant Cell Physiol 25: 1353, 1984), (6) electroporation protocols (see, e.g., Gelvin et al supra; Dekeyser et al. supra; or Fromm et al Nature 319: 791, 1986), and (7) the vortexing method (see, e.g., Kindle supra).

The following is an example outlining an Agrobacterium-mediated plant transformation. The general process for manipulating genes to be transferred into the genome of plant cells is carried out in two phases. First, all the cloning and DNA modification steps are done in *E. coli*, and the plasmid containing the gene construct of interest is transferred by conjugation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E.coli* prior to transfer to Agrobacterium for subsequent introduction into plants. Resistance genes can be carried on the vector, one for selection in bacteria, e.g., streptomycin, and the other that will express in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of Agrobacterium, delimit the region that will be transferred to the plant.

In another example, plants cells may be transformed by shooting into the cell tungsten microprojectiles on which cloned DNA is precipitated. In the Biolistic Apparatus (Bio-Rad, Hercules, Calif.) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transfer and expression of transgenes in plant cells is now routine practice to those skilled in the art. It has become a major tool to carry out gene expression studies and to attempt to obtain improved plant varieties of agricultural or commercial interest.

Transgenic Plant Regeneration

Plants cells transformed with a plant expression vector can be regenerated, e.g., from single cells, callus tissue or leaf discs according to standard plant tissue culture techniques. It is well known in the art that various cells, tissues and organs from almost any plant can be successfully cultured to regenerate an entire plant; such techniques are described, e.g., in Vasil supra; Green et al., supra; Weissbach and Weisbacch, supra; and Gelvin et al., supra.

In one particular example, a cloned ACC synthase polypeptide under the control of the 35S CaMV promoter and the nopaline synthase terminator and carrying a selectable marker (e.g., kanamycin resistance) is transformed into Agrobacterium. Transformation of leaf discs (e.g., of tobacco leaf discs), with vector-containing Agrobacterium is carried out as described by Horsch et al. (Science 227: 1229, 1985). Putative transformants are selected after a few weeks (e.g., 3 to 5 weeks) on plant tissue culture media containing kanamycin (e.g. 100 $\mu$g/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less media and grown in a greenhouse. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated on levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using ACC synthase specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant ACC synthase polypeptide is expressed in any cell or in a transgenic plant (e.g., as described above), it may be isolated, e.g., using affinity chromatography. In one example, an anti-ACC synthase antibody (e.g., produced as described in Ausubel et al., supra, or by any standard technique) may be attached to a column and used to isolate the polypeptide. Lysis and fractionation of ACC synthase-producing cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

These general techniques of polypeptide expression and purification can also be used to produce and isolate useful ACC fragments or analogs.

In other applications, however, expression of the transgene in the plant cell or the transgenic plant may be the desired result. These include applications such as ACC synthase-controlled regulation of fruit ripening or altering the normal development of the plant.

ACC Synthase Promoters

Since plant gene expression varies in accordance with developmental stages of different cell types and in response to different environmental factors and hormonal cues, the promoters (including the gene regulatory sequences) of the present invention are most useful for applications aimed at improving or engineering plant varieties of agricultural or commercial interest. As described above, crucifer ACC synthase expression is developmentally regulated during the early stages of development. It is induced by ethylene and is not responsive to auxin or wounding. Accordingly, the ACC synthase nucleic acid sequences of the present invention include regulatory sequences that promote expression of a gene in response to the phytohormone, ethylene, at specific developmental times.

To identify the minimal sequences sufficient to promote ethylene-inducible expression in immature plant tissues, functional analyses of the ACC synthase regulatory sequences are performed. These assays may be carried out using transiently transformed plant cells or transgenic plants according to standard methods (see, e.g., Gelvin et al., supra). Likely candidates for regulatory elements include those sequences shown to be important for expression of other eukaryotic genes, e.g., upstream activating sequences or enhancer elements (which may control, e.g., tissue specific or inducible expression; Wasyllyk B. CRC Rev 23, 77, 1988). Other regulatory elements useful for gene expression may include RNA processing signals, 3' terminator regions, and the gene-encoding sequence itself.

To identify particular regulatory elements of the ACC synthase promoter, 5' deletion fragments of the promoter region are constructed and analyzed in either transient assays or in vivo in transgenic plants. Construction of chimeric transgenes carrying 5' deletion fragments are produced by standard methods (see, e.g., Ausubel et al, supra). The wild-type promoter and deletion fragments are then fused to a reporter gene, for example, the $\beta$-glucuronidase gene (GUS) (see, e.g., Jefferson, Plant. Mol. Biol. Rep. 316: 387, 1987) in a plant expression vector and introduced into a host by any established method (as described above). These expression vectors are then transformed into Agrobacterium followed by transformation of the plant material, e.g., leaf discs (see, e.g., Gelvin et al. supra). Regenerated shoots are selected on medium containing, e.g., kanamycin. After rooting, transgenic plantlets are transferred to soil and grown in a growth room.

Primary transformants are then assayed for ethylene-induced GUS activity at early stages of development either by quantitating GUS activity or by histochemical staining as described below. Untransformed plants are taken as controls. Ethylene inductions can be carried out by placing the transformant in a sealed container and subjecting it to a continuous flow of approximately 1–50 L/hr or 1–100 ppm ethylene for 1–24 hrs.

Fluorometric analysis of GUS activity can be performed in any plant cell protoplast or transgenic plant according to standard methodologies. Alternatively, preparations of crude plant extracts can be assayed as described, e.g., by Jefferson (supra), using extracts standardized for protein concentration (see, e.g., Bradford, Anal. Biochem. 72: 248, 1976). GUS levels in different plant tissues are assayed by enzymatic conversion of 4-methylumbelliferyl glucuronide to 4-methylumbelliferone, which is quantified with a fluorimeter (e.g., Perkin-Elmer LS 2B, Norwalk, Conn.). Typically, the fluorimeter is set at 455 nm emission and 365 nm excitation wavelengths. GUS activity is generally expressed as picomoles per milligram of protein per minute (see, e.g., Jefferson supra).

Alternatively, GUS activity can be assayed by in situ histochemical staining, e.g., as follows. Whole tissues and thin sections from transgenic plants and untransformed control plant tissue can be stained by incubation with 5-bromo-4-chloro-3-indoyl β-D-glucuronic acid (X-gluc; Research Organics, Inc., Cleveland Ohio) as described by Jefferson et al (EMBO J 6: 3901, 1987) and Gallagher (GUS Protocols, 1992). Tissue sections are incubated at 37° C. in 2 mM X-gluc in 0.1 M $NaPO_4$ (pH 7.0), and then sectioned. GUS activity in a transformed plant is easily identified by the presence of an indigo blue precipitate within the cells expressing the reporter gene. Stained material is optionally examined microscopically using bright-field and dark-field optics.

Use

Introduction of crucifer ACC synthase into a transformed plant cell facilitates the manipulation of developmental events controlled by ethylene. For example, transgenic plants of the instant invention expressing crucifer ACC synthase might be used to alter, simply and inexpensively, ethylene biosynthesis and thereby inhibit or regulate, e.g., senescence, or fruit ripening, or any number of other plant developmental events induced by ethylene.

The instant invention also provides nucleic acid regulatory sequence elements capable of being induced by ethylene at early stages of plant development. Such sequences are useful, e.g., in transgenic plants to effect expression of a variety of recombinant proteins or RNA molecules. This expression may be controlled by ethylene induction and limited to specified periods of development.

Other Embodiments

The invention also includes any biologically active fragment or analog of a crucifer ACC synthase polypeptide. By "biologically active" is meant possessing any in vivo or in vitro activity which is characteristic of the ACC synthase polypeptide shown in FIG. 1. Because ACC synthase exhibits a range of physiological properties and because such properties may be attributable to different portions of the ACC synthase molecule, a useful ACC synthase fragment or ACC synthase analog is one which exhibits a biological activity in any biological assay for ACC synthase activity, for example, those assays described by Yang et al., supra. In particular, a biologically active ACC synthase fragment or analog possesses at least 10%, preferably 40%, and more preferably 90% of an activity of the wild-type ACC synthase polypeptide.

Preferred analogs include ACC synthase polypeptides (or biologically active fragments thereof) whose sequences differ from the wild-type sequence only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity.

Analogs can differ from naturally occurring ACC synthase polypeptide in amino acid sequence or can be modified in ways that do not involve sequence, or both. Analogs of the invention will generally exhibit at least 70%, preferably 80%, more preferably 90%, and most preferably 95% or even 99%, homology with a segment of 20 amino acid residues, preferably 40 amino acid residues, or more preferably the entire sequence of a naturally occurring ACC synthase polypeptide sequence.

Alterations in primary sequence include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule. Also included in the invention are crucifer ACC synthase polypeptides modified by in vivo or in vitro chemical derivatization of polypeptides, including acetylation, methylation, phosphorylation, carboxylation, or glycosylation.

In addition to substantially full-length polypeptides, the invention also includes biologically active fragments of the polypeptides. As used herein, the term "fragment", as applied to a polypeptide, will ordinarily be at least 20 residues, more typically at least 40 residues, and preferably at least 60 residues in length. Fragments of ACC synthase polypeptide can be generated by methods known to those skilled in the art. The ability of a candidate fragment to exhibit a biological activity of ACC synthase can be assessed by those methods described herein. Also included in the invention are ACC synthase polypeptides containing residues that are not required for biological activity of the peptide, e.g., those added by alternative mRNA splicing or alternative protein processing events. Other embodiments are within the following claims.

What is claimed is:

1. Substantially pure DNA comprising an ACC synthase promoter capable of ethylene induction and which is functional in immature plant tissues.

2. The substantially pure DNA of claim 1, wherein said promoter is a crucifer ACC synthase promoter.

3. The substantially pure DNA promoter of claim 2, wherein said promoter is obtained from a plant of the genus Arabidopsis.

4. A transgenic plant containing a transgene comprising a DNA sequence under the transcriptional control of the promoter of claim 1.

5. A transgenic seed from said transgenic plant of claim 4.

6. A transgenic cell from said transgenic plant of claim 4.

7. A method of inducibly producing a compound in a cell comprising:

providing a cell which comprises DNA encoding said compound operably linked to a promoter of claim 1; and administering ethylene to said cell to induce compound production.

8. The method of claim 7, further comprising the step of isolating said compound.

9. The method of claim 7, wherein said compound is selected from the group of a recombinant protein, a protein normally produced by said cell, and an RNA molecule.

10. The method of claim 7, wherein said cell is a plant cell.

11. The method of claim 7, wherein said promoter is a crucifer ACC synthase promoter.

12. The method of claim 11, wherein said crucifer is of the genus Arabidopsis.

13. Substantially pure DNA comprising an ACC synthase promoter which is functional in immature plant tissue.

14. The promoter of claim 13, said promoter being a crucifer ACC synthase promoter.

15. The promoter of claim 13, wherein said promoter is obtained from a plant of the genus Arabidopsis.

16. A transgenic plant containing a transgene comprising a DNA sequence under the transcriptional control of the promoter of claim 13.

17. A transgenic seed from said transgenic plant of claim 16.

18. A transgenic cell from said transgenic plant of claim 16.

* * * * *